(12) United States Patent
Peters et al.

(10) Patent No.: US 8,741,136 B2
(45) Date of Patent: Jun. 3, 2014

(54) DEVICE AND METHOD FOR TREATING OR CLEANING SAMPLE MATERIAL, IN PARTICULAR NUCLEIC ACIDS

(75) Inventors: Ralf-Peter Peters, Bergisch-Gladbach (DE); Holger Bartos, Dortmund (DE)

(73) Assignee: Boehringer Ingelheim Microparts GmbH, Dortmund (DE)

( * ) Notice: Subject to any disclaimer, the term of this patent is extended or adjusted under 35 U.S.C. 154(b) by 1141 days.

(21) Appl. No.: 12/278,817

(22) PCT Filed: Feb. 7, 2007

(86) PCT No.: PCT/EP2007/001029
§ 371 (c)(1),
(2), (4) Date: Aug. 8, 2008

(87) PCT Pub. No.: WO2007/090620
PCT Pub. Date: Aug. 16, 2007

(65) Prior Publication Data
US 2009/0209752 A1    Aug. 20, 2009

(30) Foreign Application Priority Data
Feb. 10, 2006    (DE) .......................... 10 2006 006 442

(51) Int. Cl.
| | | |
|---|---|---|
| *B01D 17/038* | (2006.01) | |
| *B01D 36/00* | (2006.01) | |
| *G01N 1/00* | (2006.01) | |
| *G01N 30/00* | (2006.01) | |
| *B04B 7/16* | (2006.01) | |
| *C12M 1/10* | (2006.01) | |
| *C12M 1/12* | (2006.01) | |

(52) U.S. Cl.
USPC ..... 210/205; 210/360.1; 210/511; 210/512.1; 422/72; 422/506; 422/533; 422/534; 366/135; 366/140; 435/289.1

(58) Field of Classification Search
USPC ................... 210/321.68, 321.69, 360.1, 369, 210/372–374, 205, 209, 411, 511, 512.1, 210/634, 781, 782, 787; 422/72, 502, 503, 422/506, 513, 533, 534; 436/177, 178, 180; 494/23, 27, 29, 36, 37; 366/135, 219, 366/220, 140; 435/287.2, 287.3, 288.4, 435/288.5, 289.1
See application file for complete search history.

(56) References Cited

U.S. PATENT DOCUMENTS 3,890,101 A    6/1975  Tiffany et al.
5,167,926 A *  12/1992  Kimura et al. ................. 422/67
(Continued)

FOREIGN PATENT DOCUMENTS

| EP | 0 211 334 A1 | 2/1987 |
| EP | 1 464 398 A2 | 10/2004 |
| WO | 2005/049206 A1 | 6/2005 |

OTHER PUBLICATIONS

International Search Report for PCT/EP2007/001029 mailed Sep. 3, 2007.

*Primary Examiner* — Joseph Drodge
(74) *Attorney, Agent, or Firm* — Michael P. Morris; Mary-Ellen M. Devlin (57) ABSTRACT

The invention relates to a device and a method for cleaning sample material, in particular nucleic acids. The cleaning process takes place by means of centrifugal microfluidics and the invention provides a simple compact construction and a simple procedure. If necessary, the sample material is easily mixed with a solvent buffer and proteases in the device. The cleaned sample material is in particular transferred directly to a container. Separate containers for the removal of excess liquid are not required.

19 Claims, 4 Drawing Sheets

(56) References Cited

U.S. PATENT DOCUMENTS

| | | |
|---|---|---|
| 6,063,589 A * | 5/2000 | Kellogg et al. ............ 435/24 |
| 6,706,519 B1 | 3/2004 | Kellogg et al. |
| 7,186,383 B2 * | 3/2007 | Webster et al. ............ 422/505 |
| 7,418,977 B2 * | 9/2008 | Ducree et al. ............ 137/825 |
| 2002/0047003 A1 | 4/2002 | Bedingham et al. |
| 2003/0064507 A1 | 4/2003 | Gallagher et al. |
| 2005/0026301 A1 | 2/2005 | Petithory |

* cited by examiner

DEVICE AND METHOD FOR TREATING OR CLEANING SAMPLE MATERIAL, IN PARTICULAR NUCLEIC ACIDS

This application is a national phase entry under 35 U.S.C. 271 of international application PCT/EP2007/001029, filed Feb. 7, 2007, which claims priority to European Application No. DE 10 2006 006 442.9, filed Feb. 10, 2006, each of which is hereby incorporated by reference in its entirety.

The present invention relates to a device and a method for treating, particularly separating, or purifying sample material, particularly nucleic acids.

The present invention is particularly concerned with microfluidic processes, systems and apparatus the structures of which range in size from about 1 to 5000 μm and/or the cavities of which each have a volume of about 1 to 5000 μl. The remarks that follow relate in particular to equipment and methods in which capillary, compressive and/or centrifugal forces come into play and are crucial to the operation.

The present invention relates particularly to the purification of sample material, most preferably nucleic acids such as DNA or RNA, which is initially present in the form of a mixture, e.g. as a sample of blood, cell culture, food or soil. The description that follows is directed primarily to the purification of nucleic acids from the sample material initially present. However, the invention is not restricted thereto. For example, other compounds such as proteins, fats or metabolites, or cells or cell constituents such as organelles can also be analysed. In addition, the apparatus and processes mentioned may also be used for other kinds of treatment of sample material or for other purposes, particularly in the field of microfluidic systems, apparatus and processes.

Up till now, the purification of sample material has been carried out either manually or using automated laboratory equipment. In manual purification, e.g. of DNA from cell culture material or blood, there is a required sequence of a number of steps that have to be carried out by an operator. These include transferring liquids into various containers and adding or removing liquids and transferring them into a centrifuge, a mixer or incubator. During purification by an automatic laboratory apparatus, these steps are carried out or automated, for example, using pipetting systems, grippers and moving devices.

A known procedure for purifying DNA envisages the following sequence, for example. 20 μl of a protease (enzyme solution) as the first treatment liquid are pipetted into a centrifuge vessel and 200 μl per sample material and 200 μl of a lysis buffer are added as the second treatment liquid. A mixer mixes the liquids together in the sealed centrifuge vessel. Then the centrifuge vessel is placed in an incubator, where it is stored for ten minutes at an elevated temperature of 56° C., for example. The centrifuge vessel is transferred into a centrifuge and subjected to centrifuging. Then the centrifuge vessel is taken out, opened, and ethanol is added as a further treatment liquid. Then further mixing and centrifuging are carried out. The centrifuging process up to this point has been used to remove drops from the inside of the container, particularly the lid or the like. The mixture (lysate) is then transferred into a so-called centrifuge column with a separating means for DNA and then centrifuged. During the centrifuging the mixture is passed through the separating means into a collecting container, DNA being bound in the separating means and the collecting container catching the filtrate. Then the collecting container is changed, the centrifuge column is opened, a washing solution, particularly a washing buffer, is added and the centrifuging process is repeated. This step is repeated with a second washing solution or a second washing buffer. Finally, the last collecting container is replaced with a clean removal container, the centrifuging column is opened and a solvent such as a particular buffer or distilled water is added and the whole thing is incubated at ambient temperature for about one minute, i.e. stored. The solvent dissolves the DNA bound to the separating means. During the subsequent centrifuging, the solvent together with the DNA is transferred into the removal container, so that the removal container holds the purified sample material, i.e. the DNA, together with the solvent without the other components, such as cell residues, breakdown products from the protein decomposition that has taken place, or the like.

The aim of the present invention is to provide an apparatus and a method for treating or purifying sample material, particularly nucleic acids, whereby the procedure and handling are simplified compared with the prior art and/or a simple, inexpensive, largely automated and/or high-speed treatment or purification of sample material is made possible.

This aim is achieved by means of an apparatus according to claim 1, 11 or 14 or a process according to claim 18 or 24. Advantageous further features are the subject of the subsidiary claims.

In a first aspect the present invention comprises using a microfluidic apparatus with an, in particular, flat or disc-shaped platform for treating or purifying the sample material. The apparatus has a sample chamber for receiving sample material, a supply chamber for holding a solvent, a reaction chamber with a separating means, particularly for the selective, reversible or temporary binding of specific sample material, such as nucleic acids, a collecting chamber especially for excess liquids and/or a removal device for holding treated or purified sample material. The chambers and the removal device are formed or mounted in or on the platform and are joined together such that the sample material can be transferred in a separating step from the first chamber through the reaction chamber into the collecting chamber, by centrifugal forces, while constituents of the sample material such as nucleic acids are retained or bound by separating means in the reaction chamber, and in a removal step the solvent is transferred by centrifugal forces into the reaction chamber, so as to dissolve bound sample material, and then transfer sample material from the reaction chamber into the removal device as treated or purified sample material. This simplifies the process substantially, as there is no need, in particular, for any change of containers and preferably no topping up or later addition of liquids such as the solvent.

Preferably, the other steps such as the mixing of the sample material with treatment liquids, particularly for protein degradation, are also carried out in the microfluidic apparatus.

Another aspect that can also be realised independently comprises incorporating the separating means, particularly a binder, filtering agent or the like, directly into the platform and allowing it to flow, in particular, perpendicularly to the plane of the plate. This results in a simple, compact construction.

A second aspect of the present invention that can also be realised independently envisages a particularly effective mixing of fluids, such as sample material with treatment liquids, while keeping the construction of the microfluidic apparatus simple. A mixing chamber is preferably connected to an additional mixing chamber solely via a channel. The fluids to be mixed are at least partly transferred into the additional mixing chamber through the channel, preferably alternately or repeatedly in succession, by centrifugal forces and are transferred from this additional mixing chamber back into the mixing chamber by gas pressure and/or resilient restoring forces. Thus, by correspondingly varying, in particular, the speed of rotation (number of revolutions or angular velocity) of the preferably flat or disc-shaped apparatus or platform, very efficient mixing is made possible. In particular, no separate mixing device is required.

A third aspect of the present invention that can also be realised independently envisages direct clamping of a container for holding treated or purified sample material on the disc-shaped rotatable platform. This container may be, in particular, a so-called Eppendorf cup or any other standard container commonly used in analysis. The direct mounting or clamping of the container to the platform dispenses with the need for an additional step of removing the treated or purified sample material and transferring it into the container.

The direct mounting of the container on the platform may also serve other purposes, for example for supplying or providing sample material or other liquids. The removal from the container and transfer into a chamber or the microfluidic channel system of the apparatus are then preferably carried out by centrifugal, compressive, gravitational and/or capillary forces.

Further advantages, features, properties and aspects of the present invention will become apparent from the claims and the following description of preferred embodiments by reference to the drawings, wherein:

In the Figures the same reference numerals have been used for identical or similar parts; corresponding or comparable properties and advantages are achieved even if the associated description has been omitted. Individual features of the different embodiments as well as the different embodiments themselves may also be combined with one another as desired and used even with differently constructed devices 1 or other processes for treating or purifying sample material.

Figure 1:
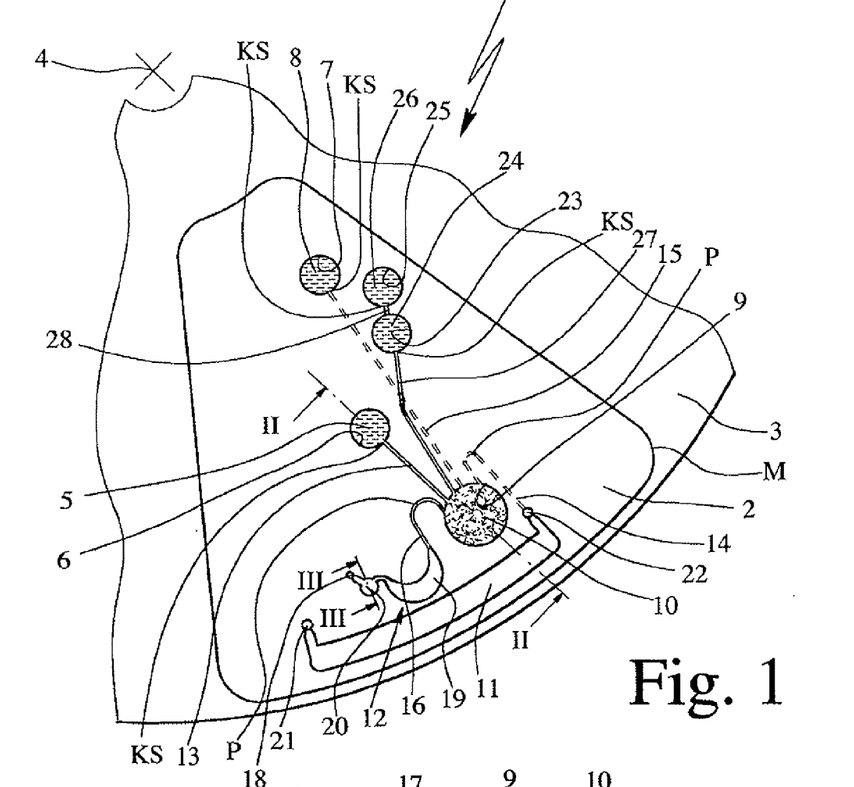
FIG. 1 shows a view, not to scale, of part of a proposed apparatus according to a first embodiment.

In a highly schematic view, not to scale, FIG. 1 shows part of an device 1 as proposed in a first embodiment. This is, in particular, a microfluidic system in the sense described hereinbefore.

The device 1 has a platform 2, which is of flat or plate-shaped construction, in particular. Preferably, the device 1 or platform 2 is in the form of a round disc, e.g. like a compact disc (CD) or the like. However, the device 1 or platform 2 may also be made up of a number of preferably segment-shaped modules M or—as in the example shown—as an individual, preferably segment-shaped module M. The module M or modules M—optionally also different modules M—is or are then capable of being mounted or clamped or used on a support 3, for example. However, other configurations and arrangements are also possible.

The device 1 or platform 2 is rotatable about a rotation axis 4 shown in FIG. 1, extending perpendicularly to the plane of the drawing in this instance, in order to generate centrifugal forces. However, here too, other arrangements are also possible. The proposed device 1 serves for the treatment, such as separation or reaction, or purification of sample material 5. The sample material 5 may be, for example, blood, blood constituents, a cell culture, a tissue sample, a food sample, a soil sample or other, particularly chemical or biological samples. Particularly preferably, the proposed device 1 and the proposed process are used for purifying nucleic acids, such as DNA or RNA, from the (crude) sample material 5 obtained initially. However, the device 1 and the processes described may also be used for other treatments, investigations or the like of the sample material 5. The foregoing remarks and those that follow apply accordingly or in supplementary fashion.

The sample material 5 is preferably in flowable or fluidisable form, particularly as a fluid, e.g. as a liquid containing cell constituents, proteins or the like. The sample material 5 will hereinafter be referred to as "liquid" for the sake of simplicity, even if it contains solid or undissolved constituents, large molecules, particularly proteins, or the like. Particularly preferably, the sample material 5 is a biological sample or constituents thereof.

In the embodiment shown, the device 1 or platform 2 comprises a sample chamber 6 for receiving sample material 5, a supply chamber 7 for holding a solvent 8, a reaction chamber 9 with a separating means 10 for in particular selectively, reversibly or temporarily binding sample material 5, particularly nucleic acids such as DNA or RNA, a collecting chamber 11 for excess sample material 5, excess liquids or the like and/or a removal device 12 for holding treated or purified sample material 5, particularly nucleic acids such as DNA or RNA or the like.

Figure 2:
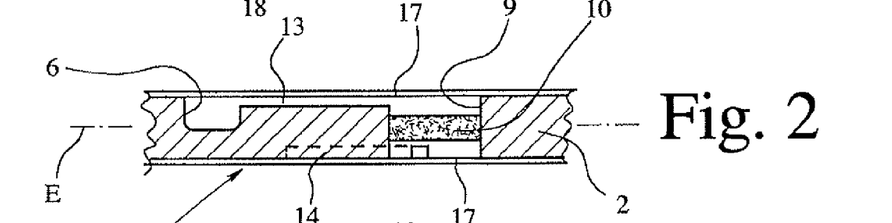
FIG. 2 shows a section through a detail of FIG. 1 on the line II-II.

FIG. 2 shows a preferred construction of the device 1. The platform 2 preferably consists of a sheet material, particularly plastics. The chambers 6, 7, 9 and 11 are preferably formed by corresponding depressions produced from one flat side or both flat sides. The channels 13 to 16 are preferably formed by corresponding grooves, channels or other recesses, particularly along the flat sides. In the embodiment shown, the channels 13 to 16 or sections thereof necessarily extend over opposite sides, e.g. so as to achieve a particularly compact arrangement of the cavities and/or desired flow properties, directions of flow or the like.

The sheet material may be produced by injection moulding, for example, and be provided with the cavities (chambers, channels, openings, recesses or the like). However, the sheet material may also be produced and/or machined in any other suitable manner.

The cavities are suitably covered by a cover 17 or—as in the embodiment shown—by covers 17 on both sides, preferably a film or the like, and are thus sealed off in fluidtight and in particular at least substantially gastight manner. Any chemicals, coatings, the separating means 10 or the like are applied, introduced or used—where necessary—before the cover is fitted.

The chambers 6, 7, 8 and 11 and the removal device 12 are arranged and/or joined together, particularly via corresponding channels 13 to 16, such that the procedure described hereinafter or a comparable procedure can take place.

In the first variant of the process, the sample material 5 is preferably pre-treated before being introduced into the sample chamber 6.

In the particularly preferred purification of nucleic acids, the pre-treatment of the sample material 5 is carried out in particular by lysing the cells originally contained in the sample material 5 and breaking down any proteins present, particularly using protease. In order to speed up or enable or optimise the breakdown of proteins the sample is preferably heated to above 50° C. for a predetermined time during the pre-treatment. In addition, during the pre-treatment, cell debris or other constituents may be separated off.

The pre-treated sample material 5 is transferred into the sample chamber 6, particularly by pipetting. The sample chamber 6 is correspondingly open in construction. Alternatively the sample may be pipetted into an open preliminary chamber (not shown) from which the sample material 5 is transferred in particular automatically by capillary forces into the sample chamber 6 which is by then closed or covered.

Moreover, the solvent 8, e.g. a so-called elution buffer or distilled water, is transferred into the supply chamber 7, particularly by pipetting. The supply chamber 7 is preferably correspondingly open in construction. However, if necessary, an open preliminary chamber (not shown) may also be used here, into which the solvent 8 is transferred or pipetted, in order to be conveyed preferably by capillary forces into the supply chamber 7 which is by then closed.

After filling with the sample material 5, which has preferably been pre-treated in this embodiment, and the solvent 8, the device 1 or platform 2 or support 3 is rotated, so as to transfer the sample material 5 by centrifugal forces from the first chamber 6 through the reaction chamber 9 into the collecting chamber 11, in a separating step, the sample material 5, or more precisely constituents of the sample material 5, in particular DNA and/or RNA, being retained and preferably bound by the separating means 10 in the reaction chamber 9.

Preferably, the separating means 10 serves to selectively, temporarily or reversibly bind sample material 5 or at least a certain component of the sample material 5. However, the separating means 10 may if necessary serve only to retain or separate off or filter sample material 5 or constituents of the sample material 5. Accordingly, the separating element 10 may also be in the form of a filter element, membrane or the like.

In the separating step, the device 1 or platform 2 is rotated at a first speed of rotation (number of revolutions or angular velocity) so as to transfer the sample material 5 from the first chamber 6 through the channel 13 and initially into the reaction chamber 9. The speed of rotation is selected so that in particular a channel or capillary stop KS—e.g. at the transition between the first chamber 6 and the channel 13—can only be overcome when the first speed of rotation is achieved or exceeded. Such a stop KS can be produced for example by a sudden enlargement in cross-section, but also by means of a suitable valve device, a membrane that bursts at a specific pressure or under a specific force, or the like.

The schematic section of a detail according to FIG. 2, along the line II-II of FIG. 1, illustrates a possible construction of the device 1 or platform 2 without sample material 5 in the region of the reaction chamber 9. The sample material 5 flows through the channel 13 into the reaction chamber 9 from above in this embodiment and is guided by the separating means 10 arranged therein. The separating means 10 preferably comprise a porous body, indicated in FIGS. 1 and/or 2, and/or glass fibres, particularly in the form of a glass fibre membrane, or the like, for selectively, temporarily or reversibly binding a component of the sample material 5 that is to be purified, especially nucleic acids. Alternatively or additionally, the separating means 10 have, or consist of, a surface coating, membrane, projections and/or the like for the desired temporary binding of at least one desired component of the sample material 5.

In the embodiment shown, the separating means 10 are preferably formed by a glass fibre membrane inserted in the reaction chamber 9, which is capable of selectively and temporarily or reversibly binding certain components of the sample material 5, especially nucleic acids. Alternatively or additionally, other microstructures, a coating, particularly an $SiO_2$ coating, so-called beads, magnetic particles or the like may also be used.

The separating means 10 may for example also comprise small bodies 38, in particular tiny spheres, so-called beads, rods or the like, preferably ranging in size from about 200 nm to 200 μm, to which the constituent of the sample material 5 which is to be purified binds. In this case, the separating means 10 then preferably also have a kind of filter 39, membrane or other suitable structure or device for retaining the small bodies 38 and in particular preventing the small bodies 38 from being carried into the collecting chamber 11.

In the embodiment shown, the sample material 5 is conveyed through the channel 14 into the collecting chamber 11 after flowing over or through the separating means. In the embodiment, the material is preferably conveyed on the side opposite the inlet, particularly in order that it flows satisfactorily through the separating means (preferably at right angles or perpendicularly to the plane of the plate E). In the embodiment shown, the channels 13 and 14 are thus arranged or formed on opposite flat sides of the platform 2 or connected to the reaction chamber 9.

The channel 14 that connects the reaction chamber 9 to the collecting chamber 11 preferably leads initially from the reaction chamber 9 to the rotation axis 4, and specifically in an arc to a point P located closest to the rotation axis 4, so that it is only possible to convey the sample material 5 from the reaction chamber 9 into the collecting chamber 11 if there is a sufficiently large amount of sample material 5 and/or other liquid available to enable the reaction chamber 9 and the adjoining channel 14 to be filled beyond the point P, so such an extent that the column of liquid extending above it causes the reaction chamber 9 to empty or the sample material 5 to be conveyed onwards into the collecting chamber 11, by means of the centrifugal forces that come into effect during rotation and optionally additional capillary forces and/or compressive forces.

After the separation step, there may be a washing step, if required, as will be explained in more detail hereinafter.

Finally, there is a removal step. Particularly preferably, there is no need for any filling, topping up or addition of the solvent 8 after the separation step, even though this is theoretically possible.

In the removal step, the speed of rotation of the device 1 is increased further, so that the solvent 8 can, in particular, overcome an optional capillary or channel stop KS and flow through the channel 15 into the reaction chamber 9. The solvent 8, particularly a so-called elution buffer, distilled water or the like, dissolves the constituents of the sample material 5, particularly nucleic acids such as DNA or RNA which have been retained, particularly bound, by the separating means 10.

Preferably, in the embodiment shown, the solvent 8 is passed through the separating means 10 from below (FIG. 2), i.e. counter to the direction in which the sample material 5 flows through the separating means 10.

The solvent 8 can then flow onwards, together with the sample material 5 dissolved by the separating means 10, i.e. the purified DNA or RNA, through the channel 16 into the removal device 12. This takes place in particular as a result of the centrifugal forces coming into effect and/or capillary and/or compressive forces.

If the separating means 10 comprise the small bodies 38 already mentioned, particularly so-called beads or the like, that bind the components of the sample material 5 that are to be purified or separated off, the solvent 8 may also serve merely to transport or otherwise deliver these bodies 38 together with the bound constituents, i.e. in particular the purified DNA or RNA, through the channel 16 into the removal device 12, or make them available. The term "solvent" is thus to be understood very broadly, as in particular there is absolutely no need for the purified or bound constituents to be dissolved from the bodies 38 or beads by the solvent 8 or in the device 1 or platform 2, even though this is theoretically possible. If necessary, the bodies 38 mentioned may also be releasably secured to a corresponding structure of the separating means 10 or filter 39 or the like and may be removable by the solvent 8.

The channel 16, like the channel 14, is preferably connected to the reaction chamber 9 on the side facing the rotation axis 4, and preferably extends initially towards the rotation axis 4, particularly in an arc, up to a point P located closest to the rotation axis 4. In contrast to the channel 14, the channel 16 or at least its connection point is preferably on the top in FIG. 1, i.e. on the flat side of the platform 2 located opposite the channels 14 and 15, at least with its section that adjoins the reaction chamber 9. As a result of this connection of the channel 16 located opposite the connection point of the channel 15, the flow through the separating means 10 is made to take place from the sample chamber 6 through the separating means 10 into the collecting chamber 11, counter to the flow of the sample material 5.

Moreover, the channel 16 preferably has an arcuate configuration, like the channel 14, although the point P of the channel 16 located closest to the rotation axis 4 is preferably at a greater distance from the rotation axis 4 than in the case of the channel 14. By suitably adjusting the volume of solvent 8 relative to the volume of sample material 5 it is possible to ensure that only the solvent 8 together with the dissolved sample material 5 flows through the channel 16 into the removal device 12. The sample material 5 initially transferred from the first chamber 6 into the reaction chamber 9 can optionally flow temporarily into the channel 16, but is in particular conveyed or sucked back through the channel 14 out of the channel 16 into the collecting chamber 11 on account of the position of the collecting chamber 11, which is radially more remote from the rotation axis 4 compared with the removal device 12, and on account of the consequently higher centrifugal forces.

Moreover, the channel 16 may be so matched in its hydrophilic or hydrophobic properties to the solvent 8 with the sample material 5 detached from the separating means 10, for example by a suitable choice of materials, coating or the like, that only the solvent 8 together with this sample material 5 flows through the channel 16 into the removal device 12.

Additionally or alternatively, a valve device (not shown) may also be used, e.g. a bursting membrane, a channel or capillary stop or the like, to ensure that only the solvent 8 with the sample material 5 detached from the separating means 10 flows through the channel 16 into the removal device 12.

Additionally or alternatively, a so-called selective vent may be used. A vent 18 associated with the channel 16 or the removal device 12 is in this case exposed or opened up, e.g. by a control fluid (not shown), by piercing, cutting or perforating the cover 17 or in some other way, only when the solvent 8 containing the purified sample material 5 is supposed to flow into the removal device 12. This exposure or opening can be effected for example by reaching or exceeding a specific speed of rotation or if a rotating apparatus (not shown) that contains the device 1 or an associated pipetting device opens the cover 17, for example, in particular by piercing the vent 18.

The removal device 12 preferably comprises a storage chamber 19 in the embodiment shown. The storage chamber 19 is preferably embodied so as to enable the concentration of the purified sample material 5, particularly the nucleic acids, to be determined optically. The purified sample material 5 can if necessary be removed directly from the storage chamber 19.

Figure 3:
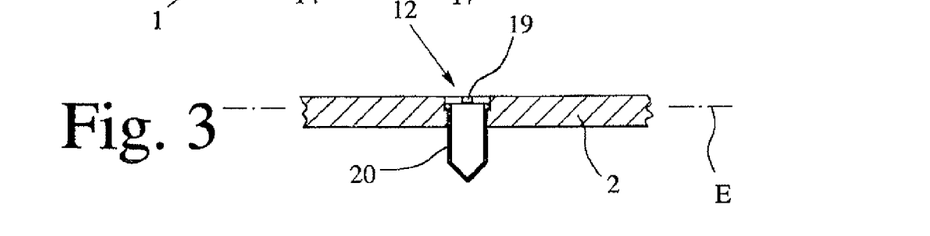
FIG. 3 shows a section through a detail of FIG. 1 on the line III-III.

Alternatively and additionally, the removal device 12 in the embodiment shown comprises a container 20 which serves to hold treated or purified sample material 5, i.e. the constituents, such as nucleic acids, detached from the separating means 10 by the solvent 8, together with the solvent 8. The container 20 is embodied in particular as a so-called Eppendorf cup or other conventional standard vessel and is preferably releasably or removably mounted on the platform 2, particularly attached thereto by clamping and/or latching, or adhesively bonded or screwed thereto, for example. The mounting is in particular such that the container 20 is held sufficiently firmly even in the presence of the centrifugal forces that occur, i.e. even during powerful rotation. For example, the platform 2 has for this purpose an opening adapted to fit the container 20 with suitable undercuts or the like, to secure the container 20, preferably by interlocking engagement, against falling out or undesirably becoming detached from the platform 2, as indicated in the schematic section through a detail in FIG. 3 along the line III-III in FIG. 1. In FIG. 3 the covers 17 have been omitted, in the interests of clarity.

In the embodiment shown, the container 20 which is, in particular, at least substantially cylindrical preferably extends transversely and in particular perpendicularly to the plane E of the disc or plate of the device 1 or platform 2.

Alternatively the container 20 may also extend substantially in or parallel to the above-mentioned plane E and/or radially with respect to the rotation axis 4.

If required, the container 20 may also be secured by a screw connection (not shown). For example, a screw or nut may be placed on the side of the platform 2 remote from the container 20 and be screwed to the container 20 to secure it by interlocking engagement on the platform 2. Moreover, the container 20 may also be screwed directly into the platform 2 or support 3 or interlockingly engage in some other way. In particular, for this purpose, the container 20 and the platform 2 or the support 3 comprise corresponding interlocking threaded portions, undercuts or the like.

The container 20 is preferably of rigid or at least stiff construction. However, the container 20 may if necessary also be a soft container such as a bag or the like. If required, it can also be arranged in a corresponding recess, e.g. under the cover 17, in the platform 2.

After the removal step—i.e. the filling of the container 20 with the purified sample material 5—the container 20 can be detached from the device 1 or platform 2, optionally by severing, cutting, breaking off, unscrewing or by some other suitable method.

The direct mounting of the container 20 on the platform 2 and filling with the treated or purified sample material 5 and/or another reaction product or the like makes handling very easy.

It should be noted that the in particular releasable mounting or clamping of the container 20 on an in particular plate- or disc-shaped platform 2 of a microfluidic device 1, which is rotatable in particular about a rotation axis 4 perpendicularly to the plane E of the plate or disc, can also be used independently of the treatment or purification of sample material 5 described hereinbefore and hereinafter, not only for receiving sample material 5 and/or other liquids, but optionally also for adding or supplying sample material 5 and/or other liquids. For example, the container 20 can then be attached to a filling or receiving chamber, e.g. the sample chamber 6 or the supply chamber 7, particularly by corresponding, preferably latching or clamping attachment to or in the chamber in question, in order to supply the respective liquid or the like. In this case, the container 20 is preferably arranged not on the underside as shown in the embodiment but on the top of the platform 2 in the position of use, to effect or assist emptying of the container 20 by gravity.

Regarding the embodiment shown it should be mentioned that the sample chamber 6 is preferably at a greater spacing from the rotation axis 4 than the supply chamber 7, i.e. is arranged radially outside it. The reaction chamber 9 which is in turn arranged radially further out is, however, arranged radially closer to the rotation axis 4 than the removal device 12 and the collecting chamber 11. The collecting chamber 11 is at a radially greater spacing from the rotation axis 4 than the removal device 12.

The collecting chamber 11 is preferably provided with a vent 21, to allow filling with the excess sample material 5 or that which has flowed through the reaction chamber 9 and optionally other liquids, as will be discussed hereinafter.

The liquids including the sample material 5 are preferably transported or conveyed substantially parallel to the plane E of the plate or disc of the platform 2, particularly on one of the two flat sides of the platform 2, in the embodiment shown.

The liquid preferably flows through the reaction chamber 9 or the separating means 10 substantially transversely or diagonally with respect to the plane E of the plate and/or substantially parallel to the rotation axis 4. This makes it possible in particular to make optimum use of the thickness of the platform 2, in order to allow the separating means 10 to extend correspondingly in this direction. This arrangement of the separating means 10, e.g. a filter, in the platform 2 and the entire flow transversely with respect to the plane E of the plate may also be used independently of the proposed device 1 in other microfluidic systems, apparatus and processes.

If necessary, it is also possible to guide the liquids including the sample material 5 from one flat side to the other. For this purpose an opening 22 is provided, for example, to connect the channel 14 extending on the underside in the embodiment shown to the collecting chamber 11 which is preferably arranged on the top.

Preferably, between the separating step and the removal step, there is at least one washing step, in this embodiment two washing steps. The device 1 or platform 2 has for this purpose at least one first receiving chamber 23 for a first washing liquid 24 and, in the embodiment shown, also a second receiving chamber 25 for a second washing liquid 26. If necessary, these can be filled with the same or different washing liquids, particularly directly or indirectly corresponding to the first chamber 6 and the supply chamber 7, preferably by pipetting or otherwise adding the washing liquid(s) 24, 26.

In particular, the washing liquid 24, 26 is a so-called washing buffer in each case.

In order to carry out the washing steps, the speed of rotation is increased, initially only to the point where only the first washing liquid 24 from the first, i.e. radially more remote receiving chamber 23 can overcome a capillary or channel stop KS or the like and can flow through a channel 27, preferably on the top, like the sample material 5, into the reaction chamber 9. The washing liquid 24 flows through the separating means 10, thus rinsing the latter. The washing liquid 24 is then conveyed onwards or transferred through the channel 14 into the collecting chamber 11, in the same way as the sample material 5.

As the speed of rotation is increased further, the second washing liquid 26 from the second receiving chamber 25 (closer to the rotation axis 4) is able to overcome an associated capillary or channel stop KS and flow through a channel 28 into the reaction chamber 9, in order to rinse the separating means 10 accordingly. In the embodiment shown, the channel 28 is connected to the first receiving chamber 23 so that the second washing liquid 26 first flows through the first receiving chamber 23 and then flows through the adjoining channel 27 to the reaction chamber 9. Instead of this serial connection, the channel 28 may, if necessary, also lead directly to the reaction chamber 9.

The number of washing steps may be varied depending on the particular requirements and application.

After the two washing steps mentioned above have been carried out, the separating means 9 are preferably dried, particularly by further centrifuging and/or gentle heating, e.g. by suitable irradiation, in the apparatus 1 or the like that rotates the device 1. Only then is the removal step carried out, which is initiated or effected by (further) increasing the speed of rotation, as described above.

The chambers 6, 7, 9, 11, 19, 23, 25 may take any desired shape as necessary and may optionally also be formed by suitably widened channels or the like. In particular, the chambers may if necessary merge continuously into adjoining channels, or vice versa.

Figure 4:
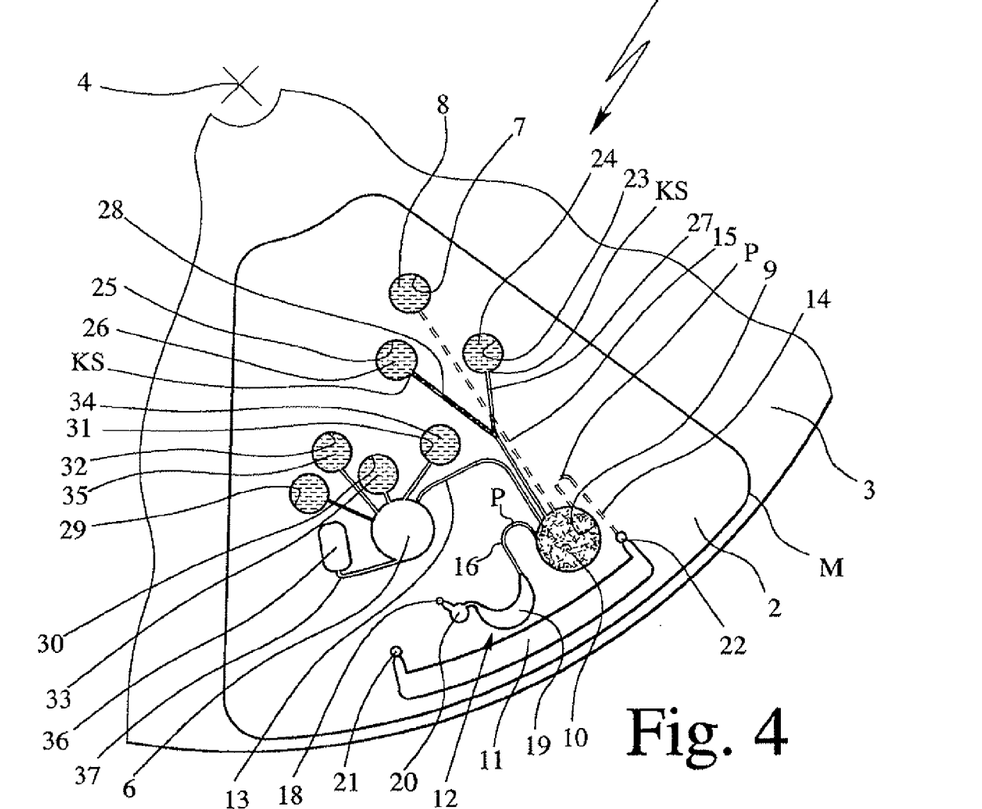
FIG. 4 shows a view, not to scale, of part of a proposed apparatus according to a second embodiment.

A second embodiment of the proposed device 1 and other variants of the process will now be described with reference to the schematic representation shown in Figure rotation axis 4 (not to scale). The description that follows is primarily restricted to new or additional aspects of the second embodiment. The remarks and explanations appearing hereinbefore are, in particular, of a supplementary or corresponding nature.

In the second embodiment, the sample chamber 6 is embodied as a mixing chamber for mixing the sample material 5 in particular with at least one first treatment liquid 33. The device 1 or platform 2 comprises further receiving chambers 29 to 32, associated with the sample or mixing chamber 6 in the second embodiment and preferably additional to the other chambers of the first embodiment.

The receiving chamber 29 serves to receive sample material 5 which if necessary has not been pre-treated, in particular has not been lysed and/or subjected to previous protein degradation in the second embodiment.

The receiving chamber 30 serves to receive a first treatment liquid 33, particularly a protease (enzyme solution), as already discussed hereinbefore.

The optional receiving chamber 31 optionally serves to receive a second treatment liquid 34, e.g. a lysing agent, as explained hereinbefore.

In addition or alternatively, other treatment liquids such as RNase A or the like may also be used, which are mixed with the sample material 5.

The receiving chamber 32 serves, in the embodiment shown, to receive another treatment liquid 35, particularly ethanol or some other solvent or transporting agent.

The filling of the receiving chambers 29 to 32 may in turn be carried out directly, e.g. by pipetting, as required. In this case, the receiving chambers 29 to 32 are open in construction. Alternatively, filling chambers (not shown) may be associated with the receiving chambers 29 to 32, from which the respective liquid or the sample material 5 is transferred, in particular by capillary forces, into the then closed chambers 29 to 32.

In the second embodiment, the receiving chamber 29 to 31 are preferably radially further away from the rotation axis 4 than the receiving chamber 32. By rotating the device 1 or platform 2 at a relatively low speed of rotation, first of all only the sample material 5 and the first and second treatment liquid 33, 34 are able to overcome associated channel or capillary stops KS and be transferred by centrifugal forces into the mixing chamber formed by the sample chamber 6. Mixing then initially takes place therein in a mixing step.

Figure 5:
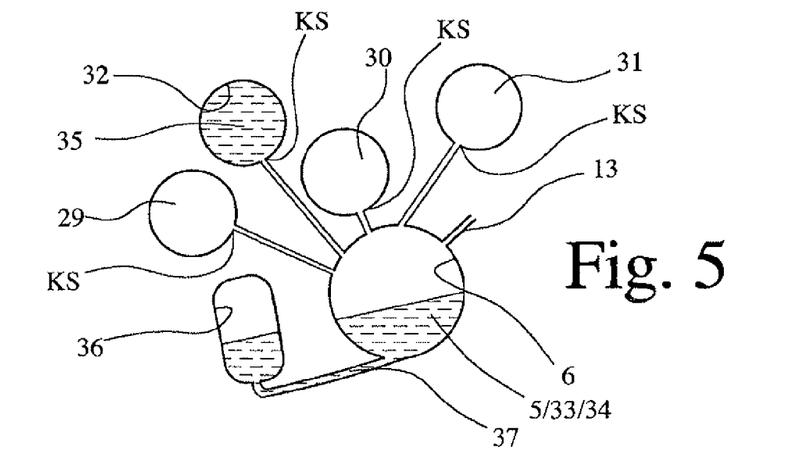
FIG. 5 shows a magnified view of a detail of FIG. 4 on the line V-V.
Figure 6:
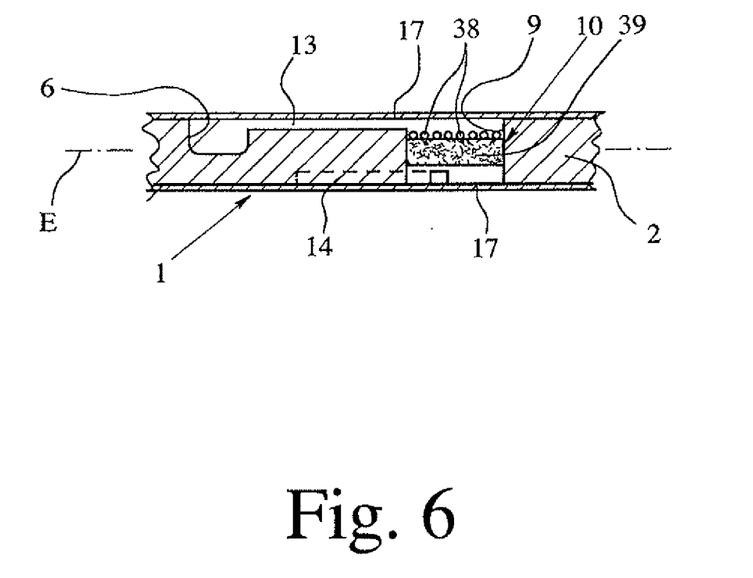
FIG. 6 shows a section through a detail of FIG. 1, corresponding to FIG. 2, in which a differently embodied separating means is provided.

The mixing is carried out, according to a particularly preferred aspect of the present invention, which can be implemented even independently of the embodiments described, by at least partly feeding the fluids that are to be mixed—in this case the sample material 5, the first treatment liquid 33 and optionally the second treatment liquid 34—through a relatively small cross-section or narrow channel 37 and/or some other device that generates turbulent currents, into an additional mixing chamber 36. In the embodiment shown, the additional mixing chamber 36 is connected to the mixing chamber 6, particularly only via the channel 37, such that the fluids that are to be mixed can be transferred through the channel 37 into the additional mixing chamber 36 by the centrifugal forces that come into effect during rotation of the device 1. FIG. 5 schematically shows this situation, in a magnified detail, in which air contained in the additional mixing chamber 36 which is preferably constructed as a blind hole has already been compressed.

By reducing the speed of rotation and hence the centrifugal forces in play or even stopping the device 1, the fluids can then be displaced or forced back out of the additional mixing chamber 36 through the channel 37 and into the mixing chamber 6 by the air pressure—i.e. gas pressure—prevailing in the additional mixing chamber 36. By suitably varying the speed of rotation and hence the centrifugal forces in play the fluids that are to be mixed are preferably alternately or repeatedly transferred out of the mixing chamber 6 and into the additional mixing chamber 36 and back again. This universal method of mixing fluids is made possible, in particular, by the fact that the channel 37 is connected to the additional mixing chamber 36 in FIG. 5 at the lowest point, i.e. the point furthest from the rotation axis 4, and is attached to the mixing chamber 6 in a region of the mixing chamber 6 that is always filled with the fluids that are to be mixed, i.e. again a region of the mixing chamber 6 which is lower or remote from the rotation axis 4.

Alternatively or additionally, the additional mixing chamber 36 may also have a resiliently deformable wall—e.g. by means of the cover 17—and/or a resiliently compressible element (not shown) for generating opposing or restoring forces that are capable of displacing the fluids which are to be mixed out of the additional mixing chamber 36 and back into the mixing chamber 6.

It should be noted that instead of centrifugal forces other compressive forces or the like may act on the fluids that are to be mixed in the mixing chamber 6, in order to be able to transfer the fluids at least partly into the additional mixing chamber 36. By suitably varying these compressive forces it is possible to achieve an alternating (partial) filling and emptying of the additional mixing chamber 36 with the fluids that are to be mixed, as described above.

The, in particular, alternate filling and emptying of the additional mixing chamber 36 with the fluids that are to be mixed, as described above, leads to very good mixing of the fluids in a simple manner. In particular there is no need for any separate mixer or the like.

After the mixing as described hereinbefore or even during the mixing, so-called incubation is preferably carried out. The sample material 5 together with the treatment liquids 33 and 34 are heated for a predetermined time to a specific temperature, e.g. for ten minutes to 56° C. This heating may be carried out, for example, using a heating device (not shown), particularly an electrically operated heater integrated in the platform 2 or cover 17, by external irradiation or in some other suitable manner. The heating is carried out in particular by the apparatus (not shown) for rotating the device 1 or an associated device. Particularly preferably, the device 1 is stopped or mixing is continued for the incubation process or during the incubation process.

The incubation serves in particular to break down protein, as protease, for example, works very effectively at the elevated temperature specified. As already explained, RNase A, for example, may also be used in addition or alternatively to the lysing agent and/or the protease, for breaking down RNA in the sample material 5.

After the mixing and incubation, the separating step is carried out. For this, the speed of rotation is increased further, so that as a result of the correspondingly increased centrifugal forces the additional treatment liquid 35, particularly ethanol, is able to overcome an associated channel or capillary stop KS or the like and flow out of the receiving chamber 32 into the mixing chamber 6. As a result of the consequent further increase in the volume of liquid in the mixing chamber 6 and in a corresponding connection of the channel 13 to the mixing chamber 6 in a region closer to the rotation axis 4, the sample material 5 together with the treatment liquids 33 to 35 can flow through the channel 13 into the reaction chamber 9, through the separating means 10 and on into the collecting chamber 11. Total or at least sufficient or substantial emptying of the mixing chamber 6 can be achieved in particular by suitable microstructuring and/or by the surface tension of the fluid mixture. However, total emptying of the mixing chamber 6 is not always possible, sensible or desirable. In particular, cell debris or other constituents may be left in the mixing chamber 6 and for example only liquid or dissolved constituents or particles up to a certain size may be separated off or removed.

Only when the speed of rotation is further increased is the first washing step carried out. This can be done by suitable design of the respective channel or capillary stops KS and/or the radial position of the respective chambers to one another.

In the second embodiment, the second receiving chamber 25 containing the second washing liquid 26 is not connected to the channel 27 via the first receiving chamber 23, but is connected to the channel 27 directly, by means of its channel 28.

Particularly preferably, the device 1 is constructed and used such that the sample material 5 and the other liquids 8, 24, 26 and 33 to 35 are all introduced, to begin with, and then the individual steps are carried out as described above, i.e. there is no need for any refilling or adding or topping up during the process. However, it is also possible to stop the device 1 after the separating step, for example, and only then to add the washing liquid(s) 24, 26 and/or the solvent 8.

The various steps or the progress of the process are controlled in particular by the speed of rotation, or by varying it. Additionally or alternatively, individual steps may also be carried out by the selective venting already mentioned in connection with the removal device 12 and/or by other effects, such as opening a valve, introducing a control liquid or by external effects, e.g. irradiation, heat, a magnetic field or electric current.

A particularly preferred embodiment will now be described, in which preferred volumes are specified:

First of all 200 µl of sample material 5, 20 µl of protease as the first treatment liquid 33, 200 µl of lysis buffer as the second treatment liquid 34 and optionally also 4 µl of RNase A are mixed together and incubated, particularly for 15 minutes at 56° C. Then 200 μl ethanol (preferably 96 to 100%) is added as an additional treatment liquid 35. The mixture or part of it, such as a supernatant, in particular without any cell debris, is then passed through the separating means 10, particularly a glass fibre membrane or the like. As the first washing liquid 24, for example 500 μl of a first washing buffer and as the second washing liquid 26 500 μl of a second washing buffer are used and passed through the separating means 10. Then centrifuging is carried out to dry the separating means 10. Finally, 200 μl of elution buffer as the solvent 8 are passed—preferably in counter-current—through the separating means 10 and transferred into the container 20 together with the eluted DNA.

The cavities in the device 1 or platform 2 are matched to the above-mentioned volumes. The above-mentioned volumes may if necessary also be up to one order of magnitude greater or one to two orders of magnitude smaller than specified. This then applies accordingly to the cavities in the device 1 or platform 2.

The proposed device 1 or platform 2 or support 3 may if necessary also be placed in a so-called swing-out rotor or some other centrifuge and for this purpose may for example have an elongate, rectangular or other suitable shape.

Figure 7:
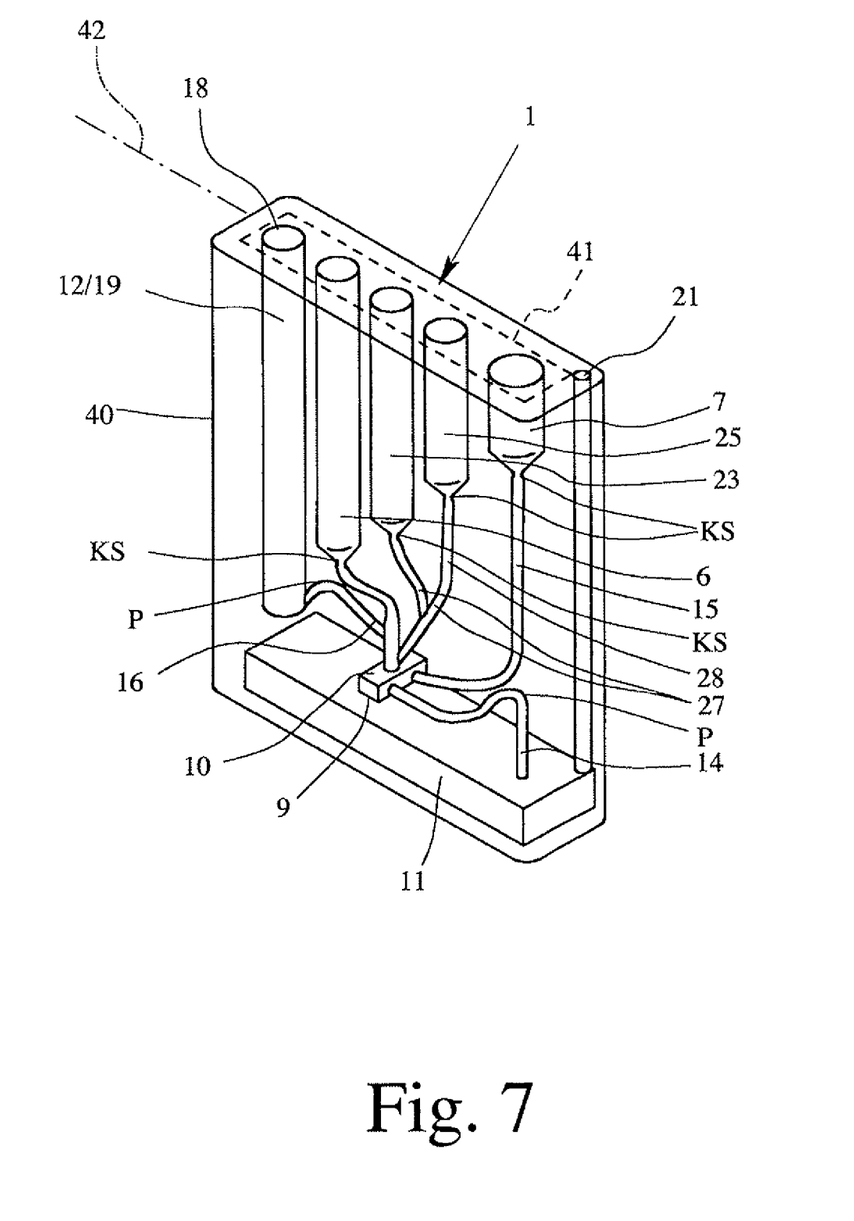
FIG. 7 shows a perspective view, not to scale, of a proposed apparatus according to a third embodiment.

As already mentioned, the proposed device 1 or platform 2 or 3 may also be used in other centrifuges or the like and/or have a different shape. As an example of this FIG. 7 shows in a schematic perspective view a third embodiment of the proposed device 1. Instead of a platform 2, a different device 40 is provided, particularly of a block-like form, which comprises the cavities of the device 1 or platform 2. Instead of the at least substantially flat arrangement in the plate-like construction, the preferably block-shaped or thick construction also allows different spatial arrangements.

The device 1 or device 40 can be inserted or mounted in a swing-out rotor (not shown) or other centrifuge, particularly in such a manner that the receiving chambers 6, 7, 23, 25 that are preferably elongate or cylindrical in the embodiment illustrated are initially substantially perpendicular and during rotation are then able to swing or pivot outwards in the direction of an axial plane with respect to the rotation axis (not shown in FIG. 7) or into the horizontal, for example about the co-rotating pivot axis 42 shown in FIG. 7.

In the embodiment shown, according to a first variant of the process, the sample material is preferably pre-treated before being introduced into the sample chamber 6.

The openings of the chambers or cavities 12, 6, 23, 25, 7 and/or 21 may be closed off if necessary, for example by plugging, by means of a removable, releasable or otherwise openable cover 41, an adhesive strip or the like.

The container 20 is not shown but may also be integrated.

The individual channels and chambers may if necessary be round, semi-circular or angular.

To avoid repetition, reference is hereby made to the foregoing remarks and explanations.

The invention claimed is:

1. A device for treating or purifying sample material, comprising:
   a sample chamber for holding sample material,
   a supply chamber for holding a solvent,
   a reaction chamber with a separating means, for the selective, reversible or temporary binding of the sample material,
   a collecting chamber, for holding excess sample material and/or other liquids,
   a removal device for holding treated or purified sample material or other treatment products,
   a rotatable platform to which the sample, supply, reaction, and collection chambers and the removal device are coupled, where the rotatable platform rotates about a rotation axis,
   a first channel of said two or more channels having originating at the reaction chamber, extending toward the rotation axis, extending through an arcuate configuration extending to a first point of inflection at a first distance from the rotation axis, and extending away from the first point of inflection and away from the rotation axis to one of the sample chamber, the supply chamber, the collection chamber and the removal device,
   a second channel originating at the reaction chamber, extending toward the rotation axis, extending through an arcuate configuration to a second point of inflection at a second distance from the rotation axis, and extending away from the second point of inflection and away from the rotation axis to one of the sample chamber, the supply chamber, the collection chamber, a supply chamber, and the removal device,
   wherein the sample material is transferred by centrifugal forces from the sample chamber through the reaction chamber into the collecting chamber, while sample material is retained or bound by the separating means in the reaction chamber, and then
   the solvent is transferred by centrifugal forces into the reaction chamber, so as to dissolve retained or bound sample material, and transfer the dissolved sample material from the reaction chamber into the removal device as treated or purified sample material.

2. The device according to claim 1, wherein the separating means comprise a porous body and/or glass fibres, a glass fibre membrane, and/or small bodies, beads, for selectively, reversibly or temporarily binding sample material or constituents thereof.

3. The device according to claim 2, wherein the device comprises at least one receiving chamber for a washing liquid, so that after the binding of sample material the separating means is rinsed at least once with washing liquid, by the centrifugal forces.

4. The device according to claim 3, wherein the device is constructed so that the solvent is passed through the separating means counter to the direction of flow of sample material and/or a washing liquid.

5. The device according to claim 4, wherein the removal device comprises a container that is detachable from the platform or device for receiving treated or purified sample material.

6. The device according to claim 5, wherein the sample chamber directly receives the sample material.

7. The device according to claim 5, wherein the sample chamber is constructed as a mixing chamber for mixing the sample material with at least one treatment liquid.

8. The device according to claim 7, wherein the device comprises a receiving chamber for receiving the sample material, a receiving chamber for receiving a first treatment liquid, a receiving chamber for receiving a second treatment liquid, and/or a receiving chamber for receiving an additional treatment liquid, wherein the sample material and/or the treatment liquid(s) are transferred by centrifugal forces into the mixing chamber.

9. The device according to claim 8, wherein the device is embodied such that the sample material and/or the first and/or second treatment liquid is transferred into the mixing chamber at or starting from a first speed of rotation and in that the additional treatment liquid is transferred into the mixing chamber at or starting from a second speed of rotation which is greater than the first.

10. The device according to claim 9, wherein the device has an additional mixing chamber which is connected to the mixing chamber only via a channel, such that the mixing process sample material is transferred alternately from the mixing chamber into the additional mixing chamber by compressive and/or centrifugal forces and is transferred back into the mixing chamber by gas pressure and/or resilient restoring forces.

11. The device according to claim 1, having a rotatable platform which comprises a mixing chamber and an additional mixing chamber, wherein the additional mixing chamber is connected to the mixing chamber via a channel such that for the mixing process the sample material is transferred from the mixing chamber into the additional mixing chamber by compressive and/or centrifugal forces and is transferred therefrom back into the mixing chamber by gas pressure and/or resilient restoring forces.

12. The device according to claim 11, wherein the additional mixing chamber is connected to the mixing chamber only via the one channel and is otherwise closed off.

13. The device according to claim 12, wherein the additional mixing chamber has a resiliently deformable wall and/or a resiliently compressible element.

14. The device according to claim 13, having a plate-shaped rotatable platform and a container which is releasably mounted on the platform for receiving treated or purified sample material.

15. The device according to claim 14, wherein the container is attached to the platform by clamping and/or latching.

16. The device according to claim 15, wherein the container extends at least substantially transversely with respect to the plane (E) of the plate or disc of the platform or parallel or radially.

17. The device according to claim 16, wherein the device or platform is embodied as a microfluidic system, in a form of a round disc, and/or is made up of segment-shaped modules (M) or forms a flat, segment-like module (M).

18. The device according to claim 1, wherein the first channel connects to said removal device.

19. The device according to claim 1, wherein said second distance is greater than the first distance.

* * * * *